United States Patent [19]

Singh

[11] 4,444,581
[45] Apr. 24, 1984

[54] ENAMINE DERIVATIVES OF PHOSPHONIC ACID ESTERS AS HERBICIDES

[75] Inventor: Rajendra K. Singh, Maryland Heights, Mo.

[73] Assignee: Monsanto Company, St. Louis, Mo.

[21] Appl. No.: 449,049

[22] Filed: Dec. 13, 1982

[51] Int. Cl.³ ..................... A01N 57/22; C07F 9/40
[52] U.S. Cl. ..................... 71/086; 260/941; 260/942
[58] Field of Search ............ 71/86; 260/942, 941

[56] References Cited

U.S. PATENT DOCUMENTS

| | | | |
|---|---|---|---|
| 4,131,448 | 12/1978 | Franz | 71/86 |
| 4,251,256 | 2/1981 | Gaertner | 71/86 |
| 4,312,662 | 1/1982 | Gaertner | 71/86 |
| 4,340,416 | 7/1982 | Dutra | 71/86 |

*Primary Examiner*—Anton H. Sutto
*Attorney, Agent, or Firm*—David Bennett; Richard H. Shear; Arnold H. Cole

[57] ABSTRACT

Novel compounds are described which are glyphosate esters having an unsaturated substituent on the nitrogen atom of the glyphosate group. The compounds are active herbicides and may provide an active ingredient of a herbicidal composition.

9 Claims, No Drawings

ENAMINE DERIVATIVES OF PHOSPHONIC ACID ESTERS AS HERBICIDES

BACKGROUND OF THE INVENTION

This invention relates to novel enamine derivatives of phosphonic acid esters and to herbicidally-effective compositions containing such derivatives.

DESCRIPTION OF INVENTION

The compounds of the invention have the formula

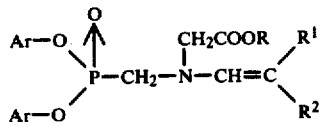

wherein the groups Ar are each individually selected from phenyl, halophenyl and $C_1$-$C_4$ alkoxyphenyl groups; R is a $C_1$ to $C_4$ alkyl group; $R^1$ is selected from the group consisting of nitrile, —COR, —COCF$_3$, and —COOR groups; and $R^2$ is selected from hydrogen, $R^1$ and COR$^3$, where $R^3$ is a $C_1$ to $C_4$ alkyl or haloalkyl group.

The compounds of the invention are effective herbicides and the invention also comprises a herbicidal composition comprising a compound of the invention as the active ingredient and a herbicidal method which comprises applying a herbicidally effective amount of such a composition to a plant.

Among the novel compounds of the invention, those in which $R^1$ is a —COOR group and $R^2$ is a —COCF$_3$ or, preferably, a —COOR group, are found to have the most attractive herbicidal properties. The preferred "Ar" groups are unsubstituted phenyl radicals and generally both "Ar" groups are identical.

The preferred compounds according to the invention include 2-propenoic acid, 2-acetyl-3-{[(diphenoxyphosphinyl)-methyl]-2-(ethoxy-2-oxoethyl)amino}, ethyl ester; 2-propenoic acid, 3-{[(diphenoxyphosphinyl)methyl](2-ethoxy-2-oxoethyl)amino-}2-(trifluoroacetyl)-, ethyl ester; and 2-propanedioc acid, ({[(diphenoxyphosphinyl)methyl](2-ethoxy-2-oxoethyl)amino}methylene), diethyl ester.

The compounds of the invention can be prepared by reaction of the corresponding glyphosate derivatives such as are described in U.S. Pat. No. 4,120,689 with an appropriate 2-ethoxy ethene derivative. A typical reaction proceeds as follows:

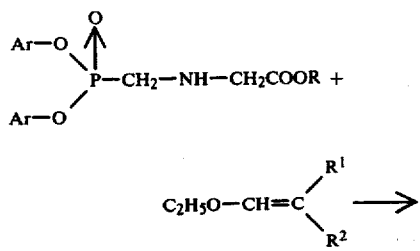

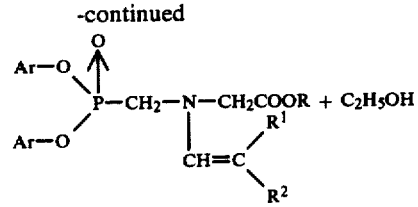

where Ar, R, $R^1$ and $R^2$ have the significances indicated above.

The reaction can be carried out by contacting the reactants in solution in an inert solvent, preferable under reflux conditions, for several hours. It is found that the reaction is assisted if carried out under an inert atmosphere (e.g., nitrogen) with continued agitation. The 2-ethoxy ethene derivative adds on to the nitrogen atom of the glyphosate derivative with the elimination of ethanol.

DESCRIPTION OF PREFERRED EMBODIMENTS

Figure 1:
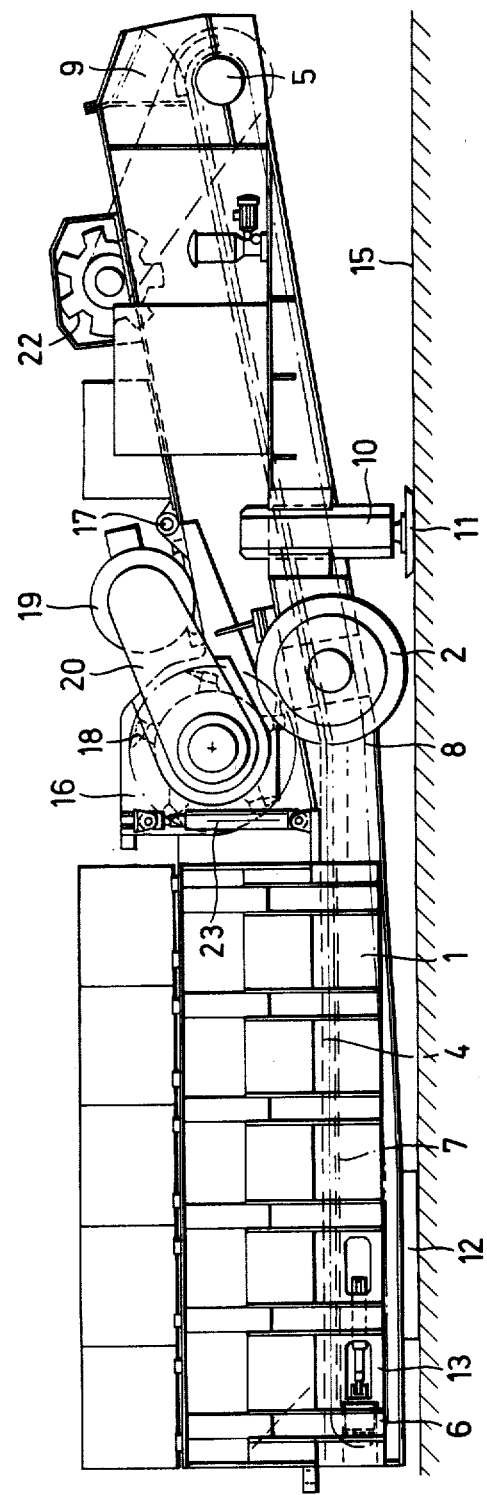
Figure 2:
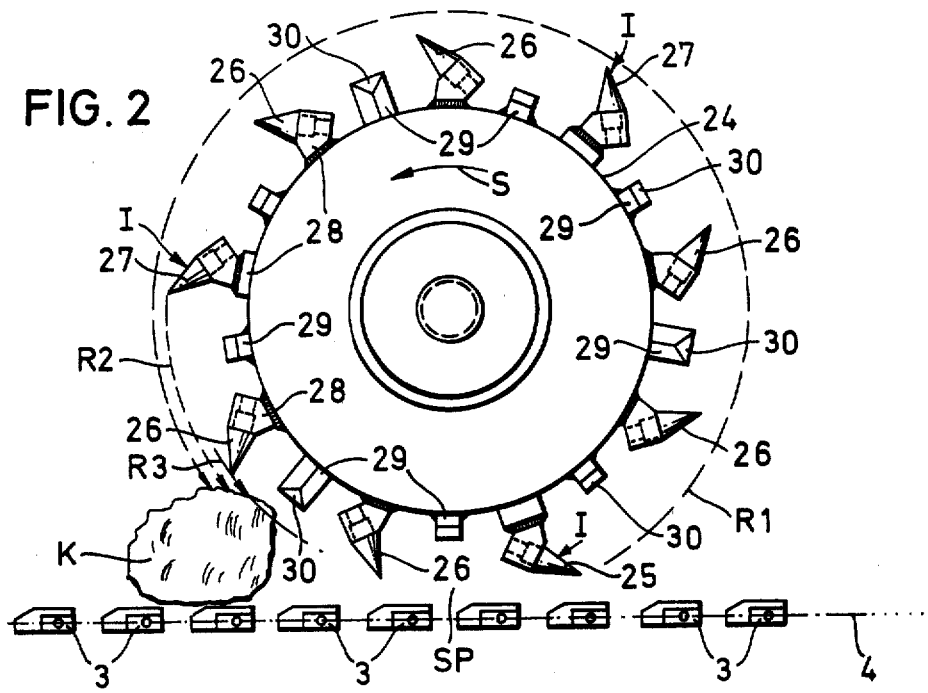
Figure 3:
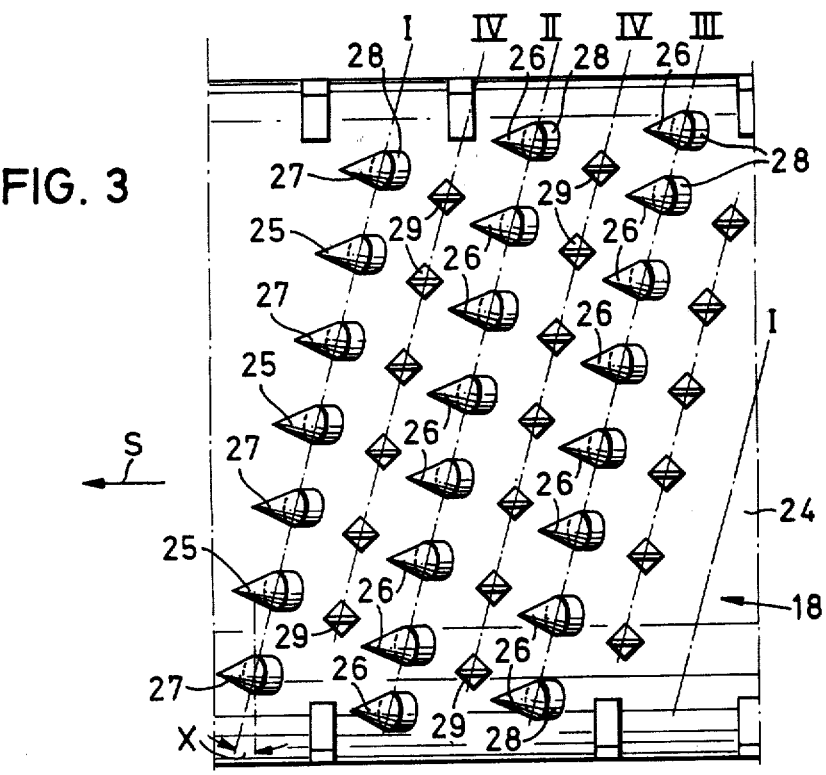
Figure 4:
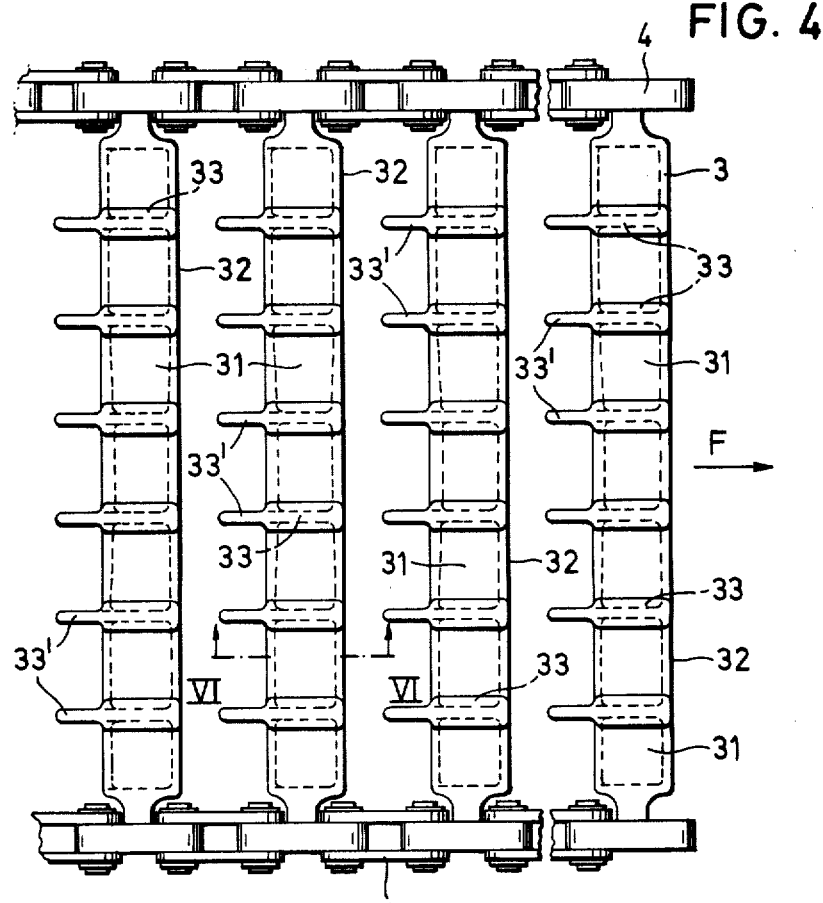
Figure 5:
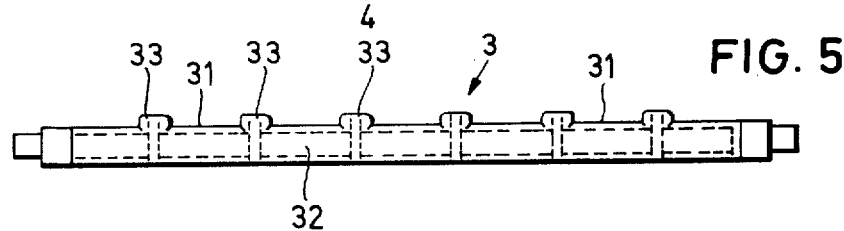
Figure 6:
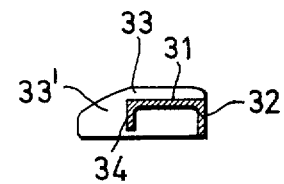

In the following Examples, the preparation of compounds according to the invention and the herbicidal properties of selected compounds is demonstrated. The Examples are for the purpose of illustration only and are intended to imply no limitation on the essential scope of the invention.

EXAMPLE 1

This Examples illustrates the preparation of a compound with the formula

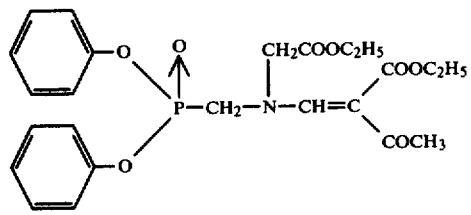

A reaction mixture comprising 5.2 gm of the ethyl ester of N-(diphenoxyphosphinylmethyl)glycine and 5.58 gm of the ethyl ester of 2-acetyl-3-ethoxy-propenoic acid in 100 ml of toluene was refluxed under nitrogen for 20 hours and then concentrated by removal of the solvent. The residue was placed in a column of 120 gm of silica gel and eluted using a 60:40 cyclohexane/ethyl acetate mixture. A purified product (3.2 gm) in the form of an oil was obtained.

The above product has an empirical formula of $C_{24}H_{28}NO_8P$. Thus, the predicted elemental proportions are: C-58.89%, H-5.77%, N-2.86%. Elemental analysis of the product showed: C-58.66%, H-5.79%, N-2.80%.

EXAMPLE 2

This Example illustrates the preparation of a compound with the formula

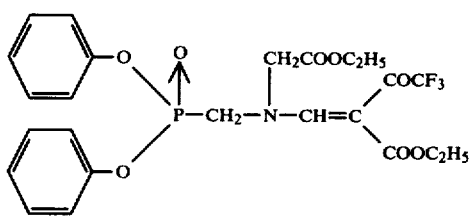

A reaction mixture comprising 6.3 gm of the ethyl ester of N-(diphenoxyphosphinylmethyl)glycine and 6.10 gm of the ethyl ester of 2-trifluoroacetyl-3-ethoxypropenoic acid in 100 ml of toluene was refluxed under nitrogen for 4½ hours. An NMR analysis of a sample of the reaction product showed very little of the starting material remained. After refluxing for a further 4 hours, the solvent was removed and the reaction mixture was placed in a chromatograph column containing 90 gm of silica gel. Elution using a 60:40 v/v mixture of cyclohexane and ethyl acetate gave 3.0 gm of an oil which upon standing solidified to material having a melting point 92°–94° C. The purified product weighed 2.85 gm.

The above compound has an empirical formula: $C_{24}H_{25}F_3NO_8P$. Theory predicts for this product: C-53.04%, H-4.64%, N-2.58%. Elemental analysis of the product showed: C-53.22%, H-4.66%, N-2.53%.

EXAMPLE 3

This Example illustrates the preparation of a compound with the formula

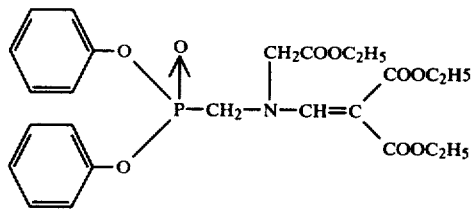

A reaction mixture comprising 5.2 g of the ethyl ester of N-(diphenoxyphosphinylmethyl)glycine and 6.48 gm of the diethyl ester of ethoxy methylene malonic acid in 100 ml of toluene was refluxed under nitrogen for 16 hours. The solvent was then removed and the product purified as described in Example 2. Elution gave first of all the malonate ester starting product (0.8 gm) and the 4.3 gm of the target product as an oil.

The above compound has an empirical formula: $C_{25}H_{30}NO_9P$. Thus, the expected elemental proportions are: C-57.8%, H-5.82%, N-2.70%. Elemental analysis of the product showed: C-57.86%, H-5.80%, N-2.70%.

EXAMPLE 4

This Example illustrates the preparation of a compound with the formula

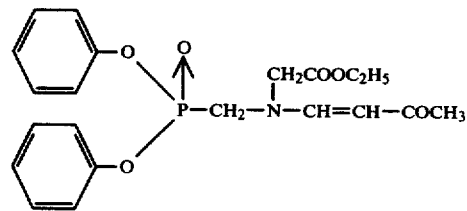

A reaction mixture comprising 7.7 gm of the ethyl ester of N-(diphenoxyphosphinylmethyl)glycine, 4.0 gm of 4-methoxy-3-butene-2-one, and 100 ml of toluene was refluxed for 18 hours under nitrogen and then concentrated by removal of toluene. The product was purified chromatographically as described in Example 2 except that the cyclohexane/ethyl acetate proportions in the elutant were 30:70. This purification resulted in 6.7 gm of product which on elemental testing was found to contain 60.37% of carbon, 5.82% of hydrogen, and 3.28% of nitrogen. The above compound has the empirical formula $C_{21}H_{24}NO_6P$ and on this basis would have predicted proportions of C-60.58%, H-5.57%, and N-3.36%.

EXAMPLE 5

This Example illustrates the herbicidal activity of the compounds of the invention described in Examples 1–4.

In each case the compound was applied in spray form to 14-day old specimens of the various plant species indicated below.

The additive was incorporated in an aqueous spray solution comprising 3 parts of cyclohexanone and 1 part of a surfactant (35 parts of the butylamine salt of dodecylbenzene-sulfonic acid and 65 parts of tall oil condensed with ethylene oxide in the ratio of 11 moles of ethylene oxide to 1 mole of tall oil).

The application rate of the spray was varied as indicated and the treated plants were placed in a greenhouse in good growing conditions. After the indicated period the effect on the plants was examined and rated according to the following index.

0 indicates 0–24% control
1 indicates 25 to 49% control
2 indicates 50 to 74% control
3 indicates 75 to 99% control
4 indicates 100% control.

The plant species tested are indicated by letter. The significances of which are as follows:
A: Canada Thistle*
B: Common Cocklebur
C: Velvetleaf
D: Morning Glory
E: Lambsquarters
F: Smartweed
G: Nutsedge* (yellow)
H: Quackgrass*
I: Johnsongrass*
J: Bromus Tectorum
K: Barnyardgrass
L: Soybean
M: Sugar Beet
N: Wheat
O: Rice
P: Sorghum
Q: Wild Buckwheat
R: Hemp Sesbania S: Panicum spp.
T: Crabgrass.
*Established from vegetative propagules.

The results obtained were as shown in Table I.

TABLE I

| Compound | WAT | kg/ha | A | B | C | D | E | F | G | H | I | J | K | L | M | N | O | P | Q | R | S | T |
|---|---|---|---|---|---|---|---|---|---|---|---|---|---|---|---|---|---|---|---|---|---|---|
| Ex. 1 | 4 | 5.6 | — | 4 | 4 | 3 | 4 | 3 | — | — | — | 3 | 4 | 4 | 4 | 4 | 4 | 4 | 3 | 4 | 4 | 4 |
|  | 4 | 1.12 | — | 4 | 4 | 3 | 4 | 4 | — | — | — | 4 | 4 | 2 | 4 | 3 | 3 | 4 | 4 | 4 | 4 | 4 |
|  | 4 | 0.28 | — | 2 | 3 | 2 | 4 | 2 | — | — | — | 2 | 3 | 1 | 3 | 3 | 3 | 3 | 3 | 4 | 3 | 4 |
|  | 4 | 11.2 | 4 | 3 | 3 | 3 | 4 | 4 | 3 | 4 | 4 | 3 | 4 | — | — | — | — | — | — | — | — | — |
|  | 4 | 5.6 | 2 | 4 | 3 | 3 | 4 | 4 | 3 | 4 | 4 | 3 | 4 | — | — | — | — | — | — | — | — | — |
| Ex. 2 | 4 | 5.6 | — | 4 | 3 | 4 | 4 | — | — | — | — | 3 | 3 | 3 | 4 | 3 | 3 | 3 | 2 | 4 | 4 | 4 |
|  | 4 | 1.12 | — | 2 | 1 | 2 | 3 | 2 | — | — | — | 2 | 3 | 1 | 1 | 2 | 1 | 3 | 1 | 1 | 3 | 3 |
|  | 4 | 11.2 | 3 | 3 | 3 | 3 | 3 | 3 | 3 | 3 | 2 | 3 | 4 | — | — | — | — | — | — | — | — | — |
|  | 4 | 5.6 | 3 | 2 | 1 | 3 | 4 | 4 | 2 | 3 | 3 | 2 | 4 | — | — | — | — | — | — | — | — | — |
| Ex. 3 | 4 | 5.6 | — | 2 | 3 | 2 | 3 | — | — | — | — | 2 | 4 | 1 | 2 | 2 | 1 | 3 | 3 | — | 3 | 4 |
|  | 4 | 1.12 | — | 2 | 1 | 2 | 3 | 2 | — | — | — | 1 | 3 | 1 | 1 | 1 | 1 | 2 | 2 | 4 | 2 | 3 |
|  | 4 | 0.28 | — | 0 | 1 | 1 | 3 | 0 | — | — | — | 0 | 3 | 1 | 1 | 1 | 1 | 2 | 0 | 3 | 1 | 2 |
|  | 4 | 11.2 | 2 | 2 | 1 | 2 | 4 | 2 | 2 | 0 | 2 | 1 | 3 | — | — | — | — | — | — | — | — | — |
|  | 4 | 5.6 | 1 | 2 | 1 | 2 | 3 | 1 | 2 | 0 | 2 | 1 | 3 | — | — | — | — | — | — | — | — | — |
| Ex. 4 | 4 | 5.6 | — | 3 | 3 | 3 | 3 | 3 |  |  |  | 0 | 3 | 1 | 2 | 2 | 2 | 3 | 3 | 1 | 3 | 4 |

*WAT indicates "Weeks After Treatment".

From the illustrative data presented above, it should be clear that the herbicidal response will be dependent upon the compound employed, the rate of application, the plant specie involved, and other factors well understood by those skilled in the art.

The herbicidal compositions (including concentrates which require dilution prior to application to the plants) of this invention contain at least one active ingredient and an adjuvant in liquid or solid form. The compositions are prepared by admixing the active ingredient with an adjuvant such as a diluent, extender, carrier or conditioning agent to provide composition in the form of a finely-divided particulate solid, pellet, solution, dispersion or emulsion. Thus, the active ingredient can be used with an adjuvant such as a finely-divided solid, a liquid of organic origin, water, a wetting agent, a dispersing agent, an emulsifying or any suitable combination of these. From the viewpoint of economy and convenience, water is the preferred diluent. However, it is found that not all the compounds are resistant to hydrolysis and in some cases this may dictate the use of non-aqueous solvent media.

The herbicidal compositions of this invention, particularly liquids and soluble powders, preferably contain as further adjuvant components one or more surface-active agents in amounts sufficient to render a given composition readily dispersible in water or in oil. The incorporation of a surface-active agent into the compositions greatly enhances their efficacy. By the term "surface-active agent" it is understood that wetting agents, dispersing agents, suspending agents, and emulsifying agents are included therein. Anionic, cationic, and nonionic agents can be used with equal facility.

Preferred wetting agents are alkyl benzene and alkyl naphthalene sulfonates, sulfated fatty alcohols, amines or acid amides, long chain acid esters of sodium isothionate, esters of sodium sulfosuccinate, sulfated or sulfonated fatty acid esters petroleum solfonates, sulfonated vegetable oils, ditertiary acetylenic glycols, polyoxyethylene derivatives of alkylphenols (particularly isooctylphenol and nonylphenol), and polyoxethylene derivatives of the mono-higher fatty acid esters of hexitol anhydrides (e.g. sorbitan). Preferred dispersants are methyl cellulose, polyvinyl alcohol, sodium lignin sulfonates, polymeric alkyl naphthalene sulfonates, sodium naphthalene sulfonate, polymethylene bisnaphthalenesulfonate, and sodium N-methyl-N- (long chain acid) laurates.

Water-dispersible powder compositions can be made containing one or more active ingredients, an inert solid extender and one or more wetting and dispersing agents. The inert solid extenders are usually of mineral origin such as the natural clays, diatomaceous earth, and synthetic minerals derived from silica and the like. Examples of such extenders include kaolinites, attapulgite clay, and synthetic magnesium silicate. Water-dispersible powders of this invention usually contain from about 5 to about 95 parts by weight of active ingredient, from about 0.25 to 25 parts by weight of wetting agent, from about 0.25 to 25 parts by weight of dispersant and from 4.5 to about 94.5 parts by weight of inert solid extender, all parts being by weight of the total composition. Where required, from about 0.1 to 2.0 parts by weight of the solid inert extender can be replaced by a corrosion inhibitor or anti-foaming agent or both.

Aqueous suspensions can be prepared by mixing together and grinding an aqueous slurry of a water-insoluble active ingredient in the presence of a dispersing agent to obtain a concentrated slurry of very finely-divided particles. The resulting concentrated aqueous suspension is characterized by its extremely small particle size, so that when diluted and sprayed, coverage is very uniform.

Emulsifiable oils are usually solutions of active ingredient in water-immiscible or partially water-immiscible solvents together with a surface active agent. Suitable solvents for the active ingredient of this invention include hydrocarbons and water-immiscible ethers, esters or ketones. The emulsifiable oil compositions generally contain from about 5 to 95 parts active ingredient, about 1 to 50 parts surface active agent and about 4 to 94 parts solvent, all parts being by weight based on the total weight of emulsifiable oil.

Compositions of this invention can also contain other additaments, for example fertilizers, phytotoxicants and plant growth regulants, pesticides and the like used as adjuvants or in combination with any of the above-described adjuvants. The compositions of this invention can also be admixed with the other materials, e.g. fertilizers, other phytotoxicants, etc., and applied in a single application. Chemicals useful in combination with the active ingredients of this invention either simultaneously or sequentially include for example triazines, ureas, carbamates, acetamides, acetanilides, uracils, acetic acids, phenols, thiolcarbamates, triazoles, benzoic acids, nitriles, and the like such as:
3-amino-2,5-dichlorobenzoic acid
3-amino-1,2,4-triazole
2-methoxy-4-ethylamino-6-isopropylamino-s-triazine
2-chloro-4-ethylamino-6-isopropylamino-s-triazine
2-chloro-N,N-diallylacetamide
2-chloroallyl diethyldithiocarbamate
N'-(4-chlorophenoxy)phenyl-N,N-dimethylurea
1,1-dimethyl-4,4'-bipyridinium dichloride
isopropyl m-(3-chlorophenyl)carbamate
2,2-dichloropropionic acid
S-2,3-dichloroallyl N,N-diisopropylthiolcarbamate
2-methoxy-3,6-dichlorobenzoic acid
2,6-dichlorobenzonitrile
N,N-dimethyl-2,2-diphenylacetamide
6,7-dihydrodipyrido(1,2-a:2',1'-c)-pyrazidinium salt
3-(3,4-dichlorophenyl)-1,1-dimethylurea
4,6-dinitro-o-sec-butylphenol
2-methyl-4,6-dinitrophenol
ethyl N,N-dipropylthiolcarbamate
2,3,6-trichlorophenylacetic acid
5-bromo-3-isopropyl-6-methyluracil
3-(3,4-dichlorophenyl)-1-methoxy-1-methylurea
2-methyl-4-chlorophenoxyacetic acid
3-(p-chlorophenyl)-1,1-dimethylurea
1-butyl-3-(3,4-dichlorophenyl)-1-methylurea
N-1-naphthylphthalamic acid
1,1'-dimethyl-4,4'-bipyridinium salt
2-chloro-4,6-bis(isopropylamino)-s-triazine
2-chloro-4,6-bis(ethylamino)-s-triazine
2,4-dichlorophenyl-4-nitrophenyl ether
alpha, alpha, alpha-trifluoro-2,6-dinitro-N,N-dipropyl-p-toluidine
S-propyl dipropylthiolcarbamate
2,4-dichlorophenoxyacetic acid
N-isopropyl-2-chloroacetanilide
2',6'-diethyl-N-methoxymethyl-2-chloroacetanilide
monosodium acid methanearsonate
disodium methanearsonate
N-(1,1-dimethylpropynyl)-3,5-dichlorobenzamide.

Fertilizers useful in combination with the active ingredients include for example ammonium nitrate, urea, potash, and superphosphate.

When operating in accordance with the present invention, effective herbicidal amounts of the compounds of the invention are applied directly or indirectly to the plants. The application of liquid and particulate solid plant regulating compositions can be carried out by conventional methods, e.g., power dusters, boom and hand sprayers, rope wick applicators, rollers, recirculating sprayers and spray dusters. The compositions can also be applied from airplanes as a dust or a spray because of their effectiveness at low dosages.

The application of a herbicidally effective amount of the compounds of this invention to the plant is essential and critical for the practice of the present invention. The exact amount of active ingredient to be employed is dependent upon the response desired in the plant as well as such other factors as the plant species, and the environmental conditions, as well as the specific compound employed. In general, the active ingredients are employed in herbicidally effective amounts equivalent to from about 0.112 to about 10.0 kg/hectare.

Although the invention is described with respect to specific modifications, the details thereof are not to be construed as limitations except to the extent indicated in the following claims.

What is claimed is:

1. A compound having the formula:

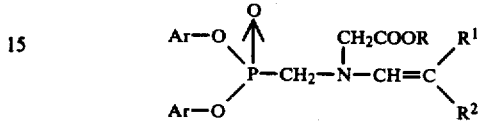

wherein the groups Ar are each individually selected from the group consisting of phenyl, halophenyl, and $C_1$–$C_4$ alkoxyphenyl radicals; R is a $C_1$ to $C_4$ alkyl group; $R^1$ is selected from the group consisting of —COOR and —COR$^3$ wherein $R^3$ is a $C_1$ to $C_4$ alkyl or haloalkyl group; and $R^2$ is selected from hydrogen and $R^1$.

2. A compound according to claim 1 in which $R^1$ is a —COOR group.

3. A compound according to claim 1 in which $R^2$ is selected from the group consisting of —COCF$_3$ and —COCH$_3$.

4. A compound according to claim 1 in which the Ar groups are each phenyl groups.

5. A compound having the formula:

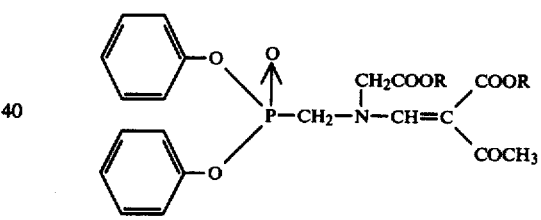

wherein R is a $C_1$ to $C_4$ alkyl group.

6. A herbicidal composition comprising from 5 to 95% by weight of a compound according to claim 1 and from 95 to 5% of adjuvant material.

7. A herbicidal composition comprising from 5 to 95% by weight of a compound according to claim 5 and from 95 to 5% of adjuvant material.

8. A herbicidal method which comprises applying to a plant a herbicidally effective amount of a composition according to claim 6.

9. A herbicidal method which comprises applying to a plant a herbicidally effective amount of a composition according to claim 7.

* * * * *